United States Patent
Hanover

(10) Patent No.: US 6,659,642 B2
(45) Date of Patent: Dec. 9, 2003

(54) NON-CIRCULAR C-ARM FOR FLUOROSCOPIC IMAGING EQUIPMENT

(75) Inventor: Barry Keith Hanover, Salt Lake City, UT (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 77 days.

(21) Appl. No.: 09/683,670

(22) Filed: Feb. 1, 2002

(65) Prior Publication Data

US 2003/0147504 A1 Aug. 7, 2003

(51) Int. Cl.[7] .................................................. H05G 1/02
(52) U.S. Cl. ..................................... 378/197; 378/193
(58) Field of Search ............................... 378/197, 193, 378/196, 198

(56) References Cited

U.S. PATENT DOCUMENTS

| | | | | |
|---|---|---|---|---|
| 4,987,585 A | * | 1/1991 | Kidd et al. ................. | 378/197 |
| 5,583,909 A | | 12/1996 | Hanover ..................... | 378/197 |

OTHER PUBLICATIONS

Euler, E. et al., (2000) "3D—Imaging with an Isocentric Mobile Arm"; Siemens Electromedica vol. 68, No. 2, pp 122–126 http://www.med.siemens.com/medroot/en/news/electro/issues/pdf/heft_2_00/english/09EULERE.PDF.*

SIREMOBIL Iso–C Breathtaking Views in the OR!—http://cg.cs.tu–berlin.de/lehre01ws/cg/uebung/ueb1/unterlagen/siremobil_iso–c–3d.pdf.*

* cited by examiner

*Primary Examiner*—Craig E. Church
*Assistant Examiner*—Courtney Thomas
(74) *Attorney, Agent, or Firm*—McAndrews, Held & Malloy, Ltd.; Peter J. Vogel; Michael A. Dellapenna

(57) ABSTRACT

A system and method of x-ray imaging is provided that includes a support base, a bearing assembly supported by the support base, and a non-circular positioning arm rotating in a semi-elliptical path relative to the support base through the bearing assembly. The non-circular positioning arm has first and second distal ends. The shape of the non-circular positioning arm conforms to a shape of a portion of a linear spiral. The system and method also includes an x-ray source located at the first distal end of the positioning arm, an x-ray detector located at the second distal end of the positioning arm. The x-ray source emits a conical beam having a theoretical central beam. The central beam passes through an origin of the linear spiral. The system also includes an imaging isocentric area located between the x-ray source and the x-ray detector. The imaging isocentric area remains substantially constant when the noncircular positioning arm rotates relative to the support base.

25 Claims, 4 Drawing Sheets

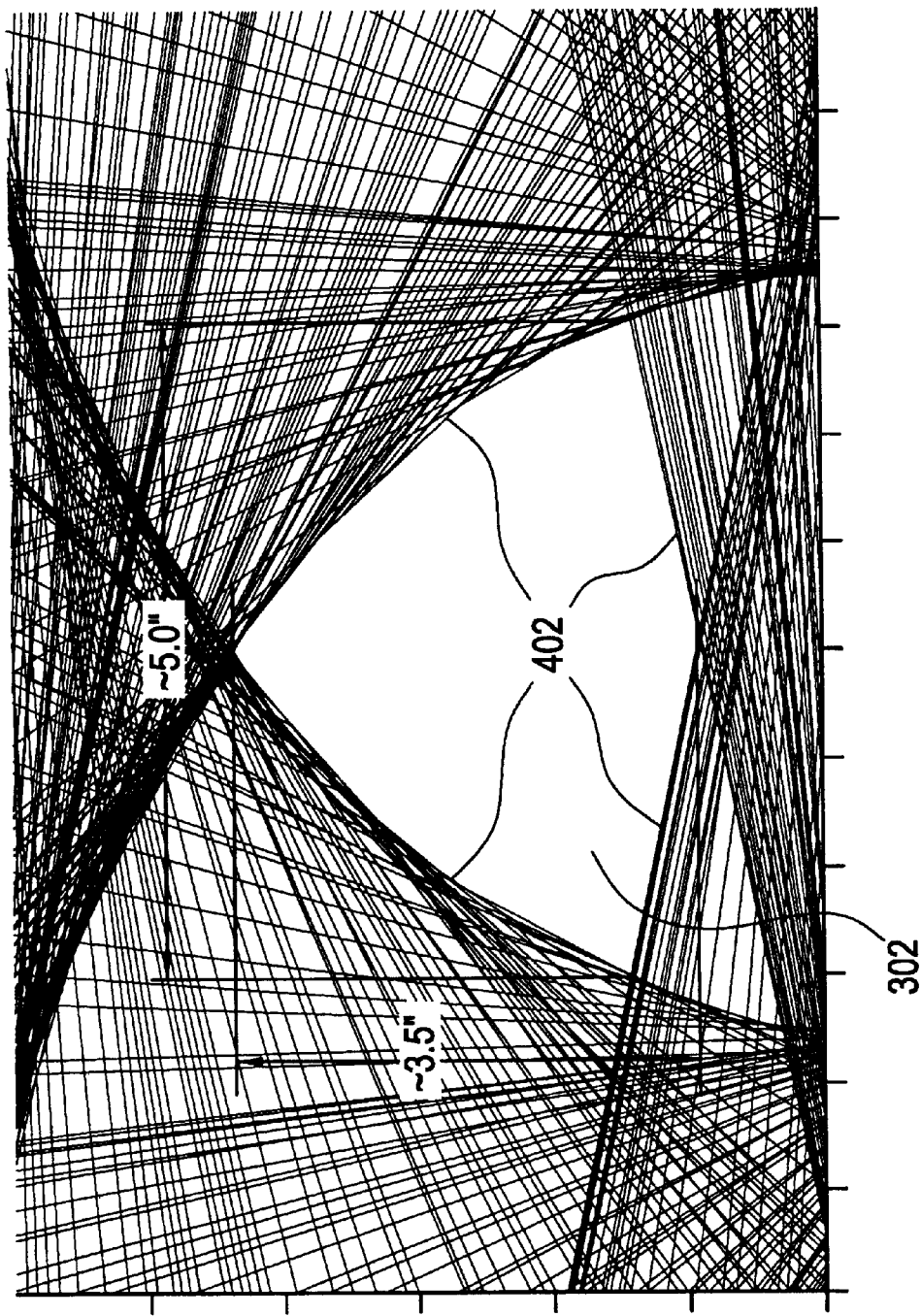

NON-CIRCULAR C-ARM FOR FLUOROSCOPIC IMAGING EQUIPMENT

BACKGROUND OF INVENTION

At least one of the embodiments of the present invention generally relates to improvements in a medical x-ray imaging system, and more particularly relates to an improved C-arm of an x-ray imaging system.

X-ray imaging systems typically include an x-ray source, a detector, and a positioning arm, such as a C-arm, supporting the x-ray source and the detector. In operation, an imaging table, on which a patient is positioned, is located between the x-ray source and the detector. The x-ray source typically emits a conical beam of radiation, such as x-rays, toward the patient. The conical beam has a theoretical central beam. The radiation typically passes through the patient positioned on the imaging table and impinges on the detector. As the radiation passes through the patient, anatomical structures of different densities inside the patient cause intensity variances in the radiation received at the detector. The detector then translates the radiation variances into an image which may be employed for clinical evaluations. Typically, the x-ray source is directly mounted to a distal end of the C-arm while the x-ray detector is mounted to another distal end of the C-arm. The x-ray source is positioned such that emitted x-rays are received by the x-ray detector.

The C-arm is typically supported by a support structure. The support structure may be mobile or fixed. The C-arm is mounted to the support structure through a bearing assembly. The bearing assembly allows the C-arm to rotate relative to the support structure. Therefore, anatomical structures of a patient positioned between the x-ray source and the x-ray detector may be imaged from different angles and perspectives. That is, the x-ray source and the x-ray detector rotate around the patient thereby imaging anatomical structures of the patient from various angles and perspectives.

Typically, C-arms are circular, or semi-circular. That is, the radii of a C-arm are the same through every angle of rotation. A circular C-arm has a true center of rotation. However, in mobile C-arm systems, the x-ray source and the x-ray detector typically are offset from the center of rotation. The x-ray source and the x-ray detector are offset in order to balance the C-arm system. That is, the x-ray source and the x-ray detector are positioned to mechanically balance out the C-arm. However, because the x-ray source and the x-ray detector are offset from the center of rotation, the central beam is also offset from the center of rotation.

Typically, when the C-arm is rotated through an arc of 180 degrees, the central beam shifts due to the offset positioning of the x-ray source and the x-ray detector. That is, when the central beam is positioned such that a target anatomical structure is within an imaging area of the conical beam, the target anatomical structure typically is not within the imaging area throughout the entire 180 degrees of C-arm rotation. That is, the conical beam is not isocentric throughout the rotation of the C-arm. Rather, because of the offset positioning, the anatomical structure does not remain within the imaging area of the conical beam.

Isocentric C-arms have been developed. For example, some systems position the x-ray source and the x-ray detector in line with the center of rotation of the circular C-arm. In order to balance the C-arm, the C-arm structure is extended past the x-ray source and the x-ray detector. The extended portions of the C-arm structure are typically heavily weighted. The C-arm is extended to counterbalance the weight of the C-arm. When the extended C-arm is rotated, however, the extended portions typically encroach upon the space of a treating physician. That is, if the C-arm is rotated in one direction, one extended portion may hit the treating physician in the head. If, however, the C-arm is rotated in the opposite direction, the other extended portion may hit the treating physician in the shins or knees. Overall, the extended, counterbalancing portions typically are bulky and cumbersome. Further, the extended portions may hinder access to the patient positioned within the C-arm. Additionally, the extended portions increase the weight of the C-arm. The increased weight of a mobile C-arm system including extended portions typically makes movement of the mobile system more difficult than if the extended portions were not included.

Instead of extending portions of the C-arm, isocentric C-arm motion may also be achieved through the use of powerful motors. That is, the x-ray source and the x-ray detector may be positioned in line with the center of rotation of the circular C-arm. While many fixed systems include expensive, powerful motors, motors may also be used with mobile systems. Powerful motors counteract the mechanical imbalance of the C-arm. The inclusion of powerful motors on mobile systems, however, increases the overall weight of the system. As stated above, increasing the weight of mobile systems decreases the ease of mobility of the system. Further, the motors are expensive.

Typically isocentric circular C-arm systems exhibit an additional limitation. While typical isocentric systems maintain an anatomical structure within an isocentric area, or imaging area, throughout 180 degrees of rotation, the distance between an x-ray detector and a patient's body in many isocentric systems fluctuates. During x-ray imaging, a patient typically lies on his back or front side. Typical systems rotate through a semi-circular arc around the patient. Therefore, because human beings typically are not round, the x-ray detector typically is closer to the patient's skin at some positions, and further away at other positions.

For example, an x-ray detector typically is closer to a patient's skin when the patient is being imaged from the side as opposed to the top or bottom. When the x-ray detector is further away from the patient's skin, the resulting images typically are of lesser quality than when the x-ray detector is closer to the patient. As the beam of a circular isocentric C-arm is rotated around a patient, the circular area of the conical beam, and therefore the magnification of the target anatomy at the isocenter, typically remain relatively constant. Because the isocenter is circular, however, an air gap results that increases between the patient's skin and the detector as the system is rotated. In some rotated positions, the air gap creates x-ray scatter. Air scatter, in turn, reduces image contrast. The further the x-ray source and x-ray detector are from the patient, the greater the air gap is between the patient's skin and the x-ray source and detector. As the air gap increases, image contrast and magnitude of magnification decrease. That is, the greater the cross-sectional area of the conical beam, the smaller the magnification of the resulting image.

Further, the patient typically is exposed to skin intensity radiation of higher magnitude when the conical beam entering the patient is more localized. Allowing the air gap to increase results in the x-ray source being closer to the patient's skin than is necessary. The close proximity of the x-ray source causes the x-rays to enter the patient through a smaller, more localized area, thereby increasing x-ray dose to the irradiated skin. Additionally, the presence of more air between the patient and the x-ray detector causes x-ray scatter and the resulting loss of image contrast.

Some systems alleviate the problems caused by an increasing air gap and less than optimal anatomical image magnification through the use of variable source-to-image distance (SID) x-ray detectors. That is, the face of the x-ray detector moves independently of the x-ray source toward and away from the patient depending on the position of the x-ray detector through the arc of rotation. Typically, variable SID is achieved through the use of an additional motor, thereby adding weight and complexity to the system. Further, the addition of the motor, and the independent movement of the x-ray detector through the rotation of the C-arm causes additional balance problems. That is, as the x-ray detector moves toward or away from the patient during the rotation of the C-arm, the center of gravity, or moment of inertia, of the C-arm changes with the additional independent movement of the x-ray detector. Overall, the cost of the system increases with the additional variable SID feature. For example, an additional motor, additional coordinating software and hardware, and additional support structures add to the cost of the system. That is, the addition of a variable SID feature to a C-arm complicates the system and increases the cost of the system.

Therefore a need has existed for a more efficient, simpler and substantially isocentric C-arm for use with fluoroscopic imaging equipment. Further, a need has existed for a less expensive, substantially isocentric C-arm. Additionally, a need has existed for a less cumbersome mobile, substantially isocentric C-arm.

SUMMARY OF INVENTION

In accordance with an embodiment of the present invention, a C-arm for an x-ray imaging system has been developed that images a target anatomical structure of a patient within an isocentric area throughout the entire range of rotation of the C-arm. The rotation of the C-arm substantially conforms to the contours of a patient's body. The x-ray imaging system includes a support base, a bearing assembly supported by the support base, a non-circular positioning arm, or C-arm, supported by the bearing assembly, an x-ray source located at a first distal end of the positioning arm; and an x-ray detector located at a second distal end of the positioning arm. The non-circular positioning arm moves arcuately with the bearing assembly to rotate the x-ray source and the x-ray detector in a semi-elliptical path relative to the support base. The x-ray source and the x-ray detector are positioned a fixed distance from each other. The distance between the x-ray source and the x-ray detector remains constant when the non-circular C-arm rotates.

The non-circular C-arm may be shaped in a linear spiral. The linear spiral is described by the equation $R=k\theta$, wherein $\theta$ is an angle of rotation, wherein R is a radius of the C-arm angle of rotation $\theta$ and wherein k is a constant. The C-arm also includes an imaging isocentric area located between the x-ray source and the x-ray detector. The imaging isocentric area remains substantially constant when the non-circular C-arm rotates relative to the support base.

In another embodiment of the present invention, a method for manufacturing a non-circular C-arm for use in an x-ray imaging system is provided. The method includes the steps of designating an arbitrary point as an origin of a reference linear spiral, forming the reference linear spiral from the origin of the reference linear spiral, determining a suitable size for a C-arm, constructing the C-arm through a portion of the reference linear spiral, and conforming the C-arm to the portion of the reference linear spiral. The determining step includes the step of determining an adequate space for imaging a human being. The constructing step includes constructing the C-arm through an approximately 190 degree portion of the linear spiral. The method also includes the step of aligning the x-ray source so that a central beam emitted from the x-ray source passes through the origin of the linear spiral and impinges on the center of the x-ray detector.

Another embodiment of the present invention provides a method for obtaining images from an x-ray system having a non-circular C-arm operating within a patient coordinate system. The non-circular C-arm carries an x-ray source at one end and an x-ray detector at an opposite end. First the method comprises the step of positioning the non-circular C-arm at a first imaging position at which the x-ray source and x-ray detector are oriented at a first angle with respect to the patient coordinate system and obtaining a first image at the first imaging position. Next, the method includes the step of rotating the non-circular C-arm from the first imaging position to a second imaging position at which the x-ray source and x-ray detector are oriented at a second angle with respect to the patient coordinate system. Then, the step of obtaining a second image at the second imaging position is performed. The rotating step includes moving the x-ray source and x-ray detector along a pseudo-elliptical path based on a shape of the non-circular C-arm. The x-ray detector is located at a proximal distance from a patient when in the first imaging position, and at a distal distance from a patient when in the second imaging position.

BRIEF DESCRIPTION OF DRAWINGS

The foregoing summary, as well as the following detailed description of the preferred embodiments of the present invention, will be better understood when read in conjunction with the appended drawings. For the purpose of illustrating the invention, there is shown in the drawings, embodiments which are present preferred. It should be understood, however, that the present invention is not limited to the precise arrangements and instrumentality shown in the attached drawings.

FIG. 4 illustrates the isocentric area of the C-arm according to an embodiment of the present invention.

DETAILED DESCRIPTION

Figure 1:
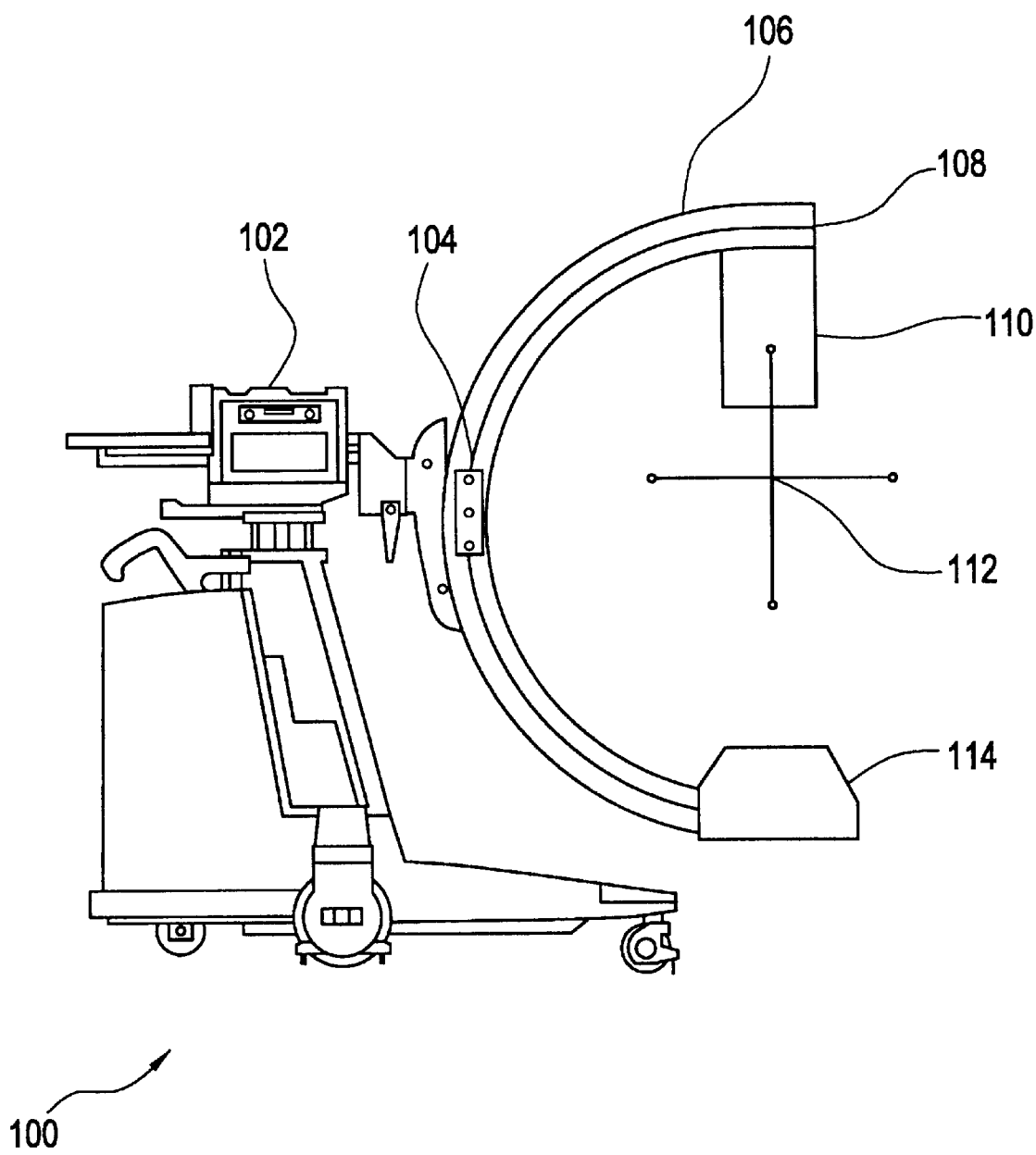
FIG. 1 illustrates an x-ray system formed in accordance with an embodiment of the present invention.

FIG. 1 illustrates an x-ray system 100 formed in accordance with an embodiment of the present invention. The x-ray system 100 includes a mobile support structure 102, a bearing assembly 104 and a positioning arm, or C-arm 106. The C-arm 106 is shaped in a non-circular shape with a track thereon such as a spiral movement track 108. An x-ray detector 110 is connected to one distal end of the C-arm 106, and an x-ray source 114 connected to another distal end of the C-arm 106. The shape of the C-arm 106 may be defined relative to an origin such as spiral origin 112. The spiral origin 112 is a virtual point located below the x-ray detector 110. The mobile support structure 102 supports the bearing assembly 104. Preferably, the C-arm 106 is in turn supported by the bearing assembly 104 at two constrained positions.

Alternatively, the C-arm 106 may contact the bearing assembly 104 at two or more positions, depending on the amount of support that is needed.

The C-arm 106 and the spiral movement track 108 may be shaped in the form of a portion of a linear spiral. A linear spiral is described by the equation R=kθ, where θ is an angle of rotation from a reference line, R is the radius from the origin 112 to a point on the spiral along an arc at an angle θ of rotation, and k is a constant. The spiral C-arm 106 is formed to follow a reference spiral according to the equation R=k θ starting at an arbitrary point in space that represents the spiral origin 112. The spiral movement track 108 illustrates a portion of the linear spiral to which the C-arm 106 conforms.

In one embodiment of the present invention, the C-arm 106 is shaped to extend through a 190 degree portion of the linear spiral. In FIG. 1, the C-arm 106 is shaped so that the x-ray detector 110 is slightly above the origin 112 of the spiral. Alternatively, the C-arm 106 may be shaped through different sections of the linear spiral when the C-arm 106 is located in a substantially vertical alignment. The shape of the C-arm 106 will vary depending upon the range of angular rotation θ of the spiral through which the C-arm extends. For example, the shape of the C-arm 106 may be defined by a portion of the linear spiral extending from θ=50 degrees to θ=240 degrees. Alternatively, the C-arm 106 shape may be defined by a portion of the linear spiral extending from θ=300 degrees to θ=390 degrees, or from θ=0 degrees to θ=190 degrees. The length of the C-arm 106 need not have a 190 degree arc. Instead, the C-arm 106 may be shorter (extending over less than a 190 degree arc of rotation) or longer (extending over more than a 190 degree arc of rotation). In the embodiment shown in FIG. 1, the 190 degree section of the linear spiral chosen for the C-arm is large enough to accommodate the imaging of a human being.

The bearing assembly 104 may be a bearing truck assembly. The bearing assembly 104 may include two bearing trucks pivotally connected to a mounting surface on the mobile support system. The C-arm 106 contacts the bearing assembly 104 at each bearing truck. Each bearing truck may include wheels or other low-friction engaging devices attached to the C-arm 106 that allow the C-arm 106 to move arcuately through the bearing assembly 104. As the C-arm 106 moves arcuately with the bearing assembly 104, the x-ray source 114 and the x-ray detector 110 move with the C-arm 106. The movement of the x-ray source 114 and the x-ray detector 110 is dictated by the C-arm 106. Further, the x-ray source 114 and the x-ray detector 110 remain at a fixed distance from each other throughout the arcuate movement, or rotation, of the C-arm 106. That is, the x-ray detector 110 does not move toward or away from the x-ray source 114 during the rotation of the C-arm 106.

Figure 2:
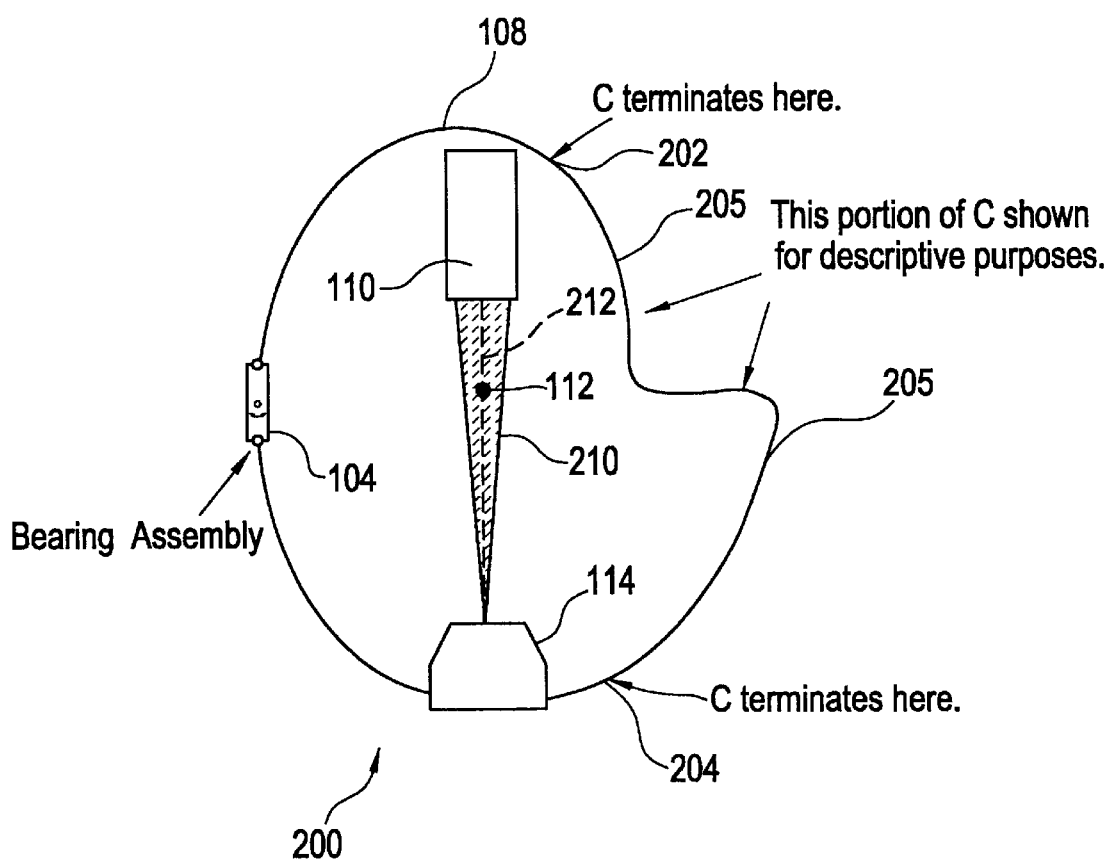
FIG. 2 is a simplified view of the x-ray system according to an embodiment of the present invention.

FIG. 2 is a simplified view 200 of the x-ray system 100 according to an embodiment of the present invention. The simplified view 200 includes an upper C-arm distal end 202, a lower C-arm distal end 204, an extended portion of the reference spiral 205, and a conical x-ray beam 210 having a central beam 212. The x-ray source 114 emits the conical beam 210 of radiation toward the x-ray detector 110. The central beam 212 of the conical beam 210 passes through the spiral origin 112. As stated above, the x-ray source 114 and the x-ray detector 110 remain a fixed distance from each other throughout rotation of the C-arm 106. Further, the central beam 212 passes through the spiral origin 112 throughout the rotation of the C-arm 106. As shown below with respect to FIG. 3, as the C-arm 106 rotates, the spiral origin 112 shifts horizontally. However, the spiral origin 112 does not shift vertically. Therefore, as long as the C-arm 106 is designed such that its center of mass is coincident with the spiral origin 112, the potential energy of the C-arm 106 does not change because the spiral origin 112, which is the center of rotation of the C-arm 106, remains on the same horizontal plane throughout the rotation of the C-arm 106. Because the potential energy of the C-arm 106 does not change throughout the rotation of the C-arm 106, the C-arm 106 remains mechanically balanced.

Figure 3:
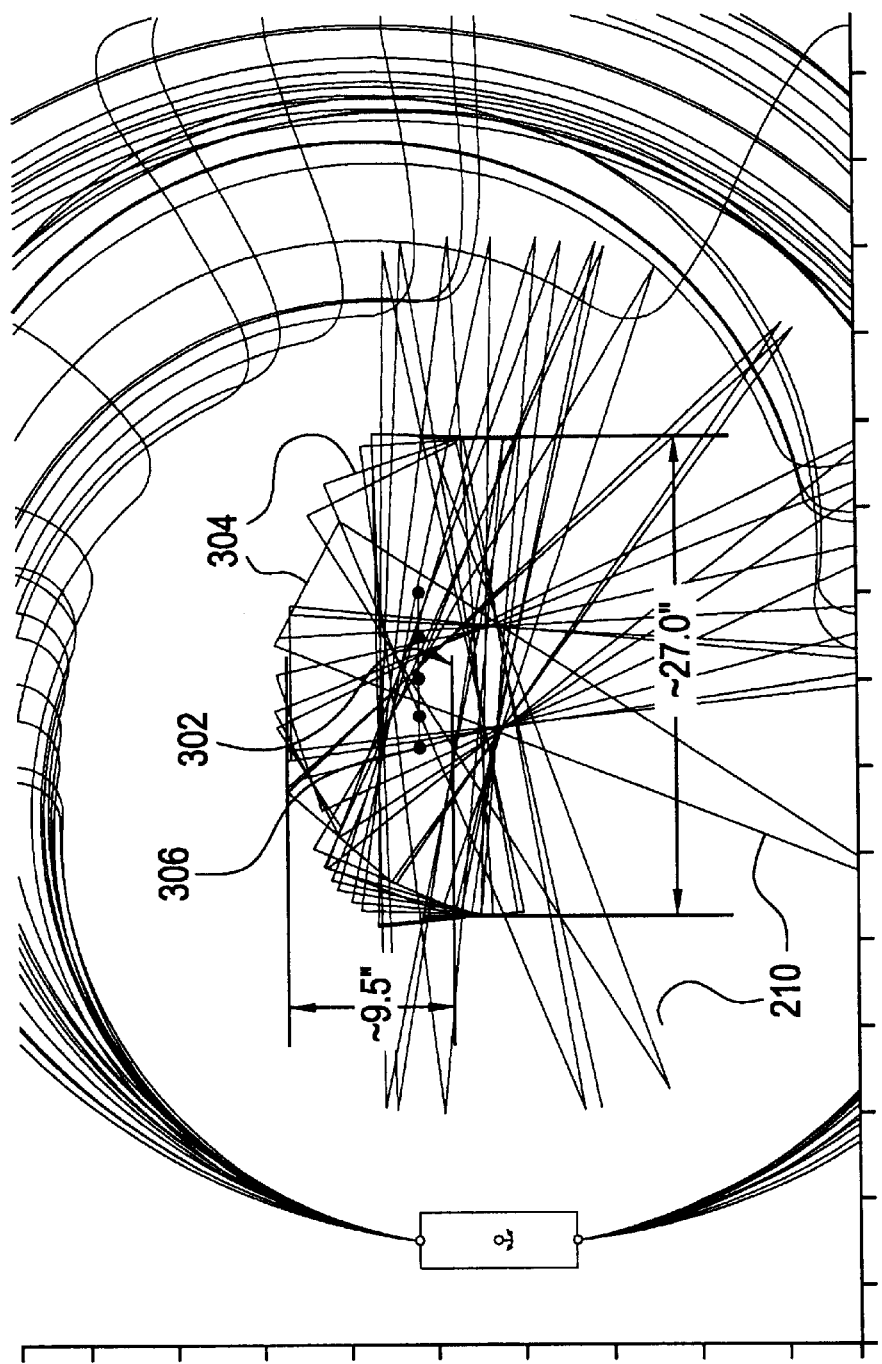
FIG. 3 illustrates the rotation of a C-arm according to an embodiment of the present invention.

FIG. 3 illustrates the rotation of a C-arm 106 according to an embodiment of the present invention. The x-ray detector 110 and the x-ray source 114 are not shown in FIG. 3. FIG. 3 illustrates a conical beam 210 shown from various rotated positions, an isocentric area 302 and a detecting surface position 304 of the x-ray detector 110 through various rotated positions. FIG. 3 also includes a horizontal dotted line 306 that represents the position of the spiral origin 112 throughout the portion of the rotation of the C-arm 106. As discussed above, the spiral origin 112 shifts horizontally, but not vertically throughout rotation of the C-arm 106.

The isocentric area 302 is an area in which a portion of the conical beam 302 remains focused on a target anatomical structure at all times throughout the rotation of the C-arm 106. Further, the outer boundaries of the conical beam 302 never cross into the isocentric area 302 during the arcuate movement, or rotation, of the C-arm 106. Because a portion of the conical beam 302 remains focused and unobstructed throughout the rotation of the C-arm 302, the isocentric area 302 primarily defines the imaging area of the x-ray system 100, when a 180° sweep of the target anatomy is desired That is, an anatomical structure to be imaged is positioned within the isocentric area 302 because a portion of the conical beam 302 remains focused on the anatomical structure throughout the rotation of the C-arm 106.

FIG. 4 illustrates the isocentric area 302 of the C-arm 106 in more detail according to an embodiment of the present invention. As discussed above, the isocentric area 302 is an area wherein a portion of the conical beam 210 remains throughout rotation of the C-arm 106. The outer boundaries 402 of the conical beam 210 do not cross into the isocentric area 302 during the C-arm 106 rotation, such as through 190 degrees. By way of example only, the isocentric area 302 may be approximately 5 inches wide at its widest portion, and approximately 3.5 inches tall at its tallest portion. However, the size and shape of the isocentric area 302 will vary.

As shown with respect to FIG. 3, the C-arm 106, and consequently the x-ray source 114 and the x-ray detector 110, rotate in a semi-elliptical, or pseudo-elliptical path. That is, because the C-arm 106 is in the shape of a linear spiral, the C-arm 106 does not rotate in a semi-circular path wherein the curvature of the C-arm 106 remains constant. Instead, the curvature of the C-arm 106 is not constant. Because the curvature of the C-arm 106 is not constant as the C-arm 106 travels through the bearing assembly 104, the radius from the center of the isocentric area 302 to the detecting surface position 304 changes throughout the rotation of the C-arm 106. For example, the radius from the center of the isocentric area 302 to the detecting surface position 304 may be greater when the x-ray detector 110 is positioned horizontally along the side of the patient as compared to when the x-ray detector 110 is positioned vertically above or below the patient. Thus, the path formed by the progression of the detecting surface position 304 throughout the entire range of rotation is semi-elliptical, or quasi-elliptical.

As shown in FIG. 3, the detecting surface position 304 of the x-ray detector 110 remains approximately within 9.5 inches vertically from the center of the isocentric area 302 and within 13.5 inches laterally from the center of the isocentric area 302. Therefore, if the target anatomical structure is within the center of the isocentric area 302, the x-ray detector 110 is closer to the anatomical structure when the x-ray detector 110 is positioned above the isocentric area 302 as opposed to along the side of the isocentric area 302.

The semi-elliptical path of the x-ray detector 110 and the x-ray source 114 conforms closer to the body contour of the patient than a semi-circular path. That is, because a patient is typically wider than he/she is thick, the x-ray detector 110 is approximately the same distance from the patient's skin when it is positioned above the patient as compared to when the x-ray detector is positioned on the side of the patient. Additionally, the cross-sectional area of the conical beam 210 on the target anatomical structure within the isocentric area 302 is larger and more focused when positioned above the patient when the C-arm 106 is rotated through a semi-elliptical path. The x-ray detector 110 conforms to the body contours of the patient more than in circular, or semi-circular C-arm systems. Therefore, the C-arm 106 of the x-ray system 100 provides better image quality and magnification because the cross-sectional area of the conical beam 210 on the target anatomical structure within the isoentric area 302 is larger and more focused where allowable by the patient's shape. Additionally, less air is present between the x-ray detector 110 and the patient.

Thus, a more efficient, simpler and substantially isocentric C-arm is provided for use with fluoroscopic imaging equipment. Additionally, a less expensive, substantially isocentric C-arm is provided. Further, a less cumbersome mobile, substantially isocentric C-arm is provided because the C-arm system does not include additional components such as motors, extensions, or computer software and hardware.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications that incorporate those features coming within the scope of the invention.

What is claimed is:

1. An x-ray imaging system including:
   a support base;
   a bearing assembly supported by said support base;
   a non-circular positioning arm shaped as a portion of a linear spiral supported by said bearing assembly, said non-circular positioning arm having first and second distal ends;
   an x-ray source located at said first distal end of said positioning arm; and
   an x-ray detector located at said second distal end of said positioning arm;
   said non-circular positioning arm moving arcuately through said bearing assembly to rotate said x-ray source and said x-ray detector in a non-circular, semi-elliptical path relative to said support base, said semi-elliptical path being defined by a shape of said non-circular positioning ann.

2. The system of claim 1 wherein said linear spiral is described by the equation R=kθ, wherein θ is an angle of rotation, wherein R is a radius of said non-circular positioning arm at angle of rotation θ and wherein k is a constant.

3. The system of claim 1 wherein said x-ray source emits a central beam, and said central beam passes through an origin of said linear spiral.

4. The system of claim 1 wherein said non-circular positioning arm has an arcuate length extending through 190 degrees of rotation, to rotate said x-ray source and said x-ray detector through 190 degrees when said non-circular positioning arm moves through said bearing assembly.

5. The system of claim 1 further including an imaging isocentric area located between said x-ray source and said x-ray detector, said imaging isocentric area remaining substantially constant when said non-circular positioning aim rotates relative to said support base.

6. The system of claim 5 wherein said non-circular positioning arm defines an isocentric area in which an imaging target is positioned.

7. The system of claim 1 wherein said non-circular positioning arm is supported by said bearing assembly at two positions.

8. The system of claim 1 wherein said x-ray source and said x-ray detector are positioned a fixed distance from each other, and wherein said fixed distance remains constant even when said non-circular positioning arm rotates.

9. The system of claim 1 wherein said x-ray system is a mobile x-ray system, wherein said support base is a mobile support base.

10. The system of claim 1 wherein said x-ray system is a fixed x-ray system.

11. A method for manufacturing a non-circular C-arm for use in an x-ray imaging system comprising:
   designating a reference linear spiral about an arbitrary origin point;
   defining radii from the origin point for initial and ending points on the reference linear spiral with respect to initial and ending rotation angles of said radii relative to a reference rotation angle;
   constructing a C-arm of described length;
   conforming the C-arm to the shape of the reference linear spiral where one end of the C-arm is located at the initial point on the reference linear spiral and an opposite end of the C-arm is located at the ending point on the reference linear spiral, such that the C-arm is configured to rotate through a non-circular arc; and
   fixing an x-ray source and detector to the C-arm.

12. The method of claim 11 wherein said defining step includes the step of forming the reference linear spiral according to an equation R=kθ, wherein θ is an angle of rotation, wherein R is a radius of said C-arm at angle of rotation θ and wherein k is a constant.

13. The method of claim 11 wherein said determining step includes the step of determining an adequate space for imaging a human being.

14. The method of claim 11 wherein said constructing step includes constructing the length of the C-arm to extend over a 190 degree arc of rotation about the linear spiral.

15. The method of claim 11 further including the step of fixing an x-ray source to a first distal end of the C-arm proximate the origin point, and fixing an x-ray detector to a second distal end of the C-arm proximate the ending point.

16. The method of claim 15 further including the step of aligning the x-ray source so that a central beam emitted from the x-ray source passes through the origin point of the reference linear spiral and impinges on the center of the x-ray detector.

17. A fluoroscopic imaging system including:

a support base;

a bearing assembly supported by said support base;

a non-circular positioning arm rotating in a non-circular, semi-elliptical path relative to said support base through said bearing assembly, said non-circular positioning arm having first and second distal ends and a shape conforming to a portion of a linear spiral, said non-circular positioning arm being shaped as a portion of a linear spiral;

an x-ray source located at said first distal end of said positioning arm;

an x-ray detector located at said second distal end of said positioning arm, said x-ray source emitting a central beam passing through an origin of said linear spiral; and an imaging isocentric area located between said x-ray source and said x-ray detector, said imaging isocentric area remaining substantially constant when said non-circular positioning arm rotates relative to said support base.

18. A method for manufacturing a non-circular C-arm for use in a fluoroscopic imaging system including the steps of:

designating an arbitrary point as an origin of a linear spiral, wherein said linear spiral is non-circular;

forming the linear spiral from the origin of the linear spiral according to the equation $R=k\theta$, wherein $\theta$ is an angle of rotation, wherein R is a radius of said non-circular positioning arm at angle of rotation $\theta$ and wherein k is a constant;

determining a suitable size for a C-arm based on a suitable imaging space for imaging an anatomical structure of a human being;

constructing the C-arm through a portion of the linear spiral;

conforming the C-arm to the portion of the linear spiral;

fixing an x-ray source to a first distal end of the C-arm, and fixing an x-ray detector to a second distal end of the C-arm; and aligning the x-ray source so that a central beam emitted from the x-ray source passes through the origin of the linear spiral and impinges on the center of the x-ray detector.

19. A method for obtaining images from an x-ray system having a non-circular C-arm operating within a patient coordinate system, said non-circular C-arm carrying an x-ray source at one end and an x-ray detector at an opposite end, the method comprising the steps of:

positioning the non-circular C-arm at a first imaging position at which the x-ray source and x-ray detector are oriented at a first angle with respect to the patient coordinate system;

obtaining a first image at the first imaging position;

rotating the non-circular C-arm along a path defined by a portion of a linear spiral from the first imaging position to a second imaging position at which the x-ray source and x-ray detector are oriented at a second angle with respect to the patient coordinate system; and obtaining a second image at the second imaging position, said rotating step moving the x-ray source and x-ray detector along a non-circular, pseudo-elliptical path based on a shape of the non-circular C-arm.

20. The method of claim 19 wherein the x-ray detector is located at a proximal distance from a patient when in the first imaging position, and at a distal distance from a patient when in the second imaging position.

21. The method of claim 19 further comprising obtaining a series of images while rotating the non-circular C-arm over an arcuate range.

22. The method of claim 19, wherein said rotating step moves the non-circular C-arm through 190 degrees of rotation.

23. An x-ray imaging system including:

a bearing assembly;

a non-circular positioning arm having first and second distal ends;

an x-ray source located at a terminal portion of said first distal end of said positioning arm; and an x-ray detector located at a terminal portion of said second distal end of said positioning arm;

said non-circular positioning arm moving arcuately through said bearing assembly to rotate said x-ray source and said x-ray detector in a non-circular, semi-elliptical path defined by a portion of a linear spiral.

24. An x-ray imaging system including:

a non-circular positioning arm having first and second distal ends, and a movement track defined by an equation $R=k\theta$, wherein $\theta$ is an angle of rotation, wherein R is a radius of said positioning arm at angle of rotation $\theta$ and wherein k is a constant; and an x-ray source and detector located at said first and second distal ends, respectively.

25. The x-ray imaging system of claim 24, wherein said positioning arm is moved manually without the use of a motor to rotate said x-ray source and said x-ray detector.

* * * * *